US009023388B2

(12) United States Patent
Xu et al.

(10) Patent No.: US 9,023,388 B2
(45) Date of Patent: *May 5, 2015

(54) FORMULATION OF SILIBININ WITH HIGH EFFICACY AND PROLONGED ACTION AND THE PREPARATION METHOD THEREOF

(75) Inventors: Ximing Xu, Jiangsu (CN); Jiangnan Yu, Jiangsu (CN); Xia Cao, Jiangsu (CN); Yuan Zhu, Jiangsu (CN)

(73) Assignee: Jiangsu University (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/126,251

(22) PCT Filed: Nov. 23, 2009

(86) PCT No.: PCT/CN2009/001300
§ 371 (c)(1),
(2), (4) Date: Apr. 27, 2011

(87) PCT Pub. No.: WO2010/075665
PCT Pub. Date: Jul. 8, 2010

(65) Prior Publication Data
US 2012/0029064 A1 Feb. 2, 2012

(30) Foreign Application Priority Data
Dec. 31, 2008 (CN) .......................... 2008 1 0242993

(51) Int. Cl.
*A61K 31/357* (2006.01)
*B29C 35/16* (2006.01)
(Continued)

(52) U.S. Cl.
CPC ............. *A61K 31/357* (2013.01); *A61K 9/1617* (2013.01); *A61K 9/1635* (2013.01);
(Continued)

(58) Field of Classification Search
None
See application file for complete search history.

(56) References Cited

U.S. PATENT DOCUMENTS

2003/0069302 A1* 4/2003 Zielinski ........................ 514/452
2005/0064034 A1* 3/2005 Li et al. .......................... 424/469
(Continued)

FOREIGN PATENT DOCUMENTS

CN 101164537 A * 4/2008
EP 1499895 B1 * 5/2008

OTHER PUBLICATIONS

Li et al., Controlled release of avermectin from porous hollow silica nanoparticles: Influence of shell thickness on loading efficiency, UV-shielding property and release, Journal of Controlled Release, 111 (2006) 81-88.*
(Continued)

*Primary Examiner* — Rachael E Bredefeld
*Assistant Examiner* — Dominic Lazaro
(74) *Attorney, Agent, or Firm* — Schmeiser, Olsen & Watts, LLP (57) ABSTRACT

A high-efficacy, long-acting formulation of silibinin, comprising silibinin solid dispersion, silibinin-loaded silica nanoparticles, slow-release matrix material and release enhancer, wherein the mass ratio of these components is silibinin solid dispersion:silibinin-loaded silica nanoparticles:slow-release matrix material:release enhancer=1:0.5~1.25:0.1~0.3: 0.1~0.3; the drug loading rate of the said silibinin-loaded silica nanoparticles is 51.29~51.77%; the said silibinin solid dispersion contains povidone K30, soybean lecithin, acrylic resin IV, wherein the mass ratio between silibinin and other medical accessories is silibinin:povidone K30:soybean lecithin:acrylic resin IV=1:1~3:0.3~0.8:0.2~0.5. Compared with the existing formulations, the half life of the high-efficacy, long-acting formulation of silibinin disclosed in this invention is 14.8 times longer while the mean residence time (MRT) of which is 4.52 times longer; when tested in vivo in Beagle dogs, this new formulation of silibinin presents a smoother concentration-time curve and reaches the continuous release for 72 hours. This invention discloses its preparation method.

10 Claims, 2 Drawing Sheets

(51) Int. Cl.
  *B82Y 5/00* (2011.01)
  *B82Y 40/00* (2011.01)
  *A61K 9/16* (2006.01)
  *A61K 9/20* (2006.01)
  *A61K 9/48* (2006.01)

(52) U.S. Cl.
  CPC ............ *A61K9/1652* (2013.01); *A61K 9/2027* (2013.01); *A61K 9/2054* (2013.01); *A61K 9/2068* (2013.01); *A61K 9/2095* (2013.01); *A61K 9/4866* (2013.01); *A61K 9/4875* (2013.01); *Y10S 977/773* (2013.01); *Y10S 977/888* (2013.01); *Y10S 977/906* (2013.01)

(56) References Cited

U.S. PATENT DOCUMENTS

2006/0057206 A1* 3/2006 Wong et al. ................... 424/473
2006/0068022 A1* 3/2006 Playford ....................... 424/535

OTHER PUBLICATIONS

Scholfield, Composition of Soybean Lecithin, J. Am. Oil Chem. Soc., 58 (1981) 889-892.*

Abarkan et al., Tailored macro/microstructural properties of colloidal silica nanoparticles via microemulsion preparation, Polyhedron 25 (2006) 1763-1770.*

Huang et al., Single w/o microemulsion templating of CdS nanoparticles, J. Mater. Sci 39 (2004) 2411-2415 (Huang), EP 1 499 895 B1 to Tan et al.*

Zhu et al., Poly(L-lysine)-modified silica nanoparticles for the delivery of antisense oligonucleotides, Biotechnol. Appl. Biochem., 39 (2004) 179-187.*

Li et al., Fabrication of porous hollow silica nanoparticles and their applications in drug release control, J. Control. Release, 98 (2004) 245-254.* e et al., Solubilities of Salicylic Acid in Supercritical Carbon Dioxide with Ethanol Cosolvent, J. Supercrit. Fluids, 1996, 9, 82-87.*

English language translation of CN 101164537.*

Li et al., Controlled release of avermectin from porous hollow silica nanoparticles: Influence of shell thickness on loading efficiency, UV-shielding property and release, Journal of Controlled Release, 111 (2006) 81-88 (Li II).*

Scholfield, Composition of Soybean Lecithin, J. Am. Oil Chem. Soc., 58 (1981) 889-892 (Scholfield).*

Abarkan et al., Tailored macro/microstructural properties of colloidal silica nanoparticles via microemulsion preparation, Polyhedron 25 (2006) 1763-1770 (Abarkan).*

Huang et al., Single w/o microemulsion templating of CdS nanoparticles, J. Mater. Sci 39 (2004) 2411-2415 (Huang).*

Zhu et al., Poly(L-lysine)-modified silica nanoparticles for the delivery of antisense oligonucleotides, Biotechnol. Appl. Biochem., 39 (2004) 179-187 (Zhu).*

Li et al., Fabrication of porous hollow silica nanoparticles and their applications in drug release control, J. Control. Release, 98 (2004) 245-254 (Li III).*

Ke et al., Solubilities of Salicylic Acid in Supercritical Carbon Dioxide with Ethanol Cosolvent, J. Supercrit. Fluids, 1996, 9, 82-87 (Ke).*

Dow, Methocel Food Gums, Product Brochure; accessed Dec. 19, 2014.*

Dow, Using Dow Excipients for Controlled Release of Drugs in Hydrophilic Matrix Systems, 2006; accessed Dec. 22, 2014.*

* cited by examiner

FORMULATION OF SILIBININ WITH HIGH EFFICACY AND PROLONGED ACTION AND THE PREPARATION METHOD THEREOF

FIELD OF THE INVENTION

This invention relates to a high-efficacy, long-acting drug formulation and its preparation method, and particularly to a high-efficacy, long-acting formulation of silibinin and its preparation method that enable silibinin to function 72 hours continuously in a slow-release mode.

BACKGROUND OF THE INVENTION

Silibinin (SLB) is a flavonoid compound extracted from the fruit of *silybum marianum*, a plant of the Asteraceae. In virtue of its prominent function in protecting and stabilizing liver cells, Silibinin presents remarkable therapeutic effect in treatment of many liver diseases. It has been becoming an ideal drug for restoring liver health, and being widely used in clinical treatment of acute and chronic hepatitis, hepatic fibrosis and early hepatic cirrhosis [see: Flora K, Hahn M, Rahn H, et, al. "Milk Thistle (*silybum marianum*) for the Therapy of Liver Diseases." *Am J Gastroenterol* 93.13 (1998): 139]. However, the oral bioavailability of silibinin remains considerably low due to its poor solubility in water. In recent years, the research on new dosage forms and preparation methods of silibinin focuses on increasing its oral bioavailability, for example, preparing it in the form of lecithin complex, solid dispersion or cyclodextrin inclusion compound [see: Giacomellis S, Gallo D, Apollonio P, et, al. "Silybin and Its Bioavailable Phospholipid Complex (IdB 1016) Potentiate in vitro and in vivo the Activity of Cisplatin." *Life Sci* 70.12 (2002):1447; Li Fengqian, Hu Jinhong, Zhu Quangang, et, al. "Determination of Total Flavonoids in Silibinin Solid Dispersion." *Chinese Traditional and Herbal Drugs* 33.1 (2002): 31; Li Fengqian, Hu Jinhong, Wang Hui, et, al. "Solubilization and Lattice Changing Effect of PEG 6000 Solid Dispersion System on Poorly Soluble Silymarin." *Pharmaceutica Sinica* 37.4 (2002):294; Lirussi F, Beccarello A, Zanette G, et, al. "Silybin-beta-cyclodextrin in the Treatment of Patients with Diabetes Mellitus and Alcohol Liver Disease: Efficacy Study of a New Preparation of an Antioxidant Agent." *Diabets Nutr Metab* 15.4 (2003):222.].

Compared with other said methods, solid dispersion technique is more extensively utilized in virtue of its simple preparation procedure and outstanding solubilization effect [see: Deng Li, et, al. "Research on Preparation methods and in vitro Dissolution of Silymarin Solid Dispersion." *Journal of the Second Military Medical University* 21.10 (2000):961.; Wei Zhenping, Mao Shirui, Bi Dianzhou, et, al. "Dissolution Improvement of Cisapride by Solid Dispersion with HPMC," *Journal of Chinese Pharmaceutical Science* 13.4 (2004):254.; Cui Fude, Yang Mingshi, Jiang Yanyan. "Design of Sustained-release Nitrendipine Microspheres Having Solid Dispersion Structure by Quasi-emulsion Solvent Diffusion Method." *Journal of Controlled Release* 97.3 (2003): 375.]. When being prepared in the form of solid dispersion, the solubility and dissolution rate of the poorly soluble drug are enhanced, which consequently improve absorbability of the drug and increase its bioavailability. But such defects of the insoluble drug as frequent administrations and big difference between peak and trough concentrations remain unchanged. Controlled release preparation of drugs is being widely used in virtue of its less total amount and frequency of administration, which consequently avoids peak and trough phenomenon of plasma concentration, reduces toxic and side effects and improves patients' adaptability. Therefore, the defects such as great fluctuation of plasma concentration and frequent administrations of the poorly soluble drug can be effectively avoided when the drug is prepared in slow-release form after having been solubilized. [see: Lee K, Nguyen T, Hanley T, et, al. "Nanostructure of Liquid Crystalline Matrix Determines in vitro Sustained Release and in vivo Oral Absorption Kenetics for Hydrophilic Model Drugs." *International Journal of Pharmaceutics* 365.1-2 (2009):190.; Wang Jiexin, Wang Zhihui, Chen Jianfeng, et, al. "Direct Encapsulation of Water-soluble Drug into Silica Microcapsules for Sustained Release Applications." *Materials Research Bulletin* 43.12 (2008): 3374.].

In recent years, much attention has been attracted to the special structure and features of the mesoporous material. It refers to a type of material containing multiple pores with diameter between 2 to 50 nanometers. A mesoporous material can be disordered or ordered according to the structure of the mesopores. The ordered mesoporous material enjoys the following structural characteristics: 1. long-range structure being ordered; 2. pore size distribution being narrow and adjustable between 1.5 to 10 nanometers; 3. specific surface area reaching as high as 1000 m2/g; 4. high porosity and 5. rich unsaturated radicals on its surface. When used as a drug carrier, the ordered mesoporous material presents the following advantages: 1. being nontoxic, nonphysioactive and biocompatible; 2. having evenly distributed, adjustable pore canals, within which its rich silanic radicals act as active sites for combining organic guest molecules; the drug molecules, through combining with these radicals, distribute within the canals evenly as well. Since the drug is absorbed within the ordered mesoporous material, it acts in a slow-release mode; 3. protecting the integrity of molecular structure of the drug. Therefore, an ideal controlled release can be achieved for the hydrophobic drug when the mesoporous material is adopted as the controlled release carrier. The release effect varies in relation to the structure of the pore canal of the ordered mesoporous material.

On the basis of "triple release" mechanism comprising quick-release of the solid dispersion, regular slow-release of the hydrophilic gel matrix and the long-acting slow-release of the ordered mesoporous material, this invention is intended to prepare a 72-hour controlled release formulation of silibinin encompassing both quick-release and double slow-release, and presenting double pharmacokinetic effects of high-efficacy and long action.

DESCRIPTION OF THE INVENTION

Solid dispersion technique, ordered mesoporous nanoparticle technique and hydrophilic gel matrix technique are combinedly adopted in this invention in order to prepare a 72-hour controlled release, high-efficacy, long-acting formulation of silibinin characteristic of high bioavailability and smooth in vivo release.

The technical solution provided in this invention includes:
A high-efficacy, long-acting formulation of silibinin, comprising silibinin solid dispersion, silibinin-loaded silica nanoparticles, slow-release matrix material and release enhancer, wherein the mass ratio of these components is silibinin solid dispersion:silibinin-loaded silica nanoparticles:slow-release matrix material:release enhancer=1:0.5~1.25:0.1~0.3:0.1~0.3; the drug loading rate of the said silibinin-loaded silica nanoparticles is 51.29~51.77%; the said silibinin solid dispersion contains povidone K30, soybean lecithin, acrylic resin IV, wherein the mass ratio between silibinin and other medical accessories is silibinin:povidone K30:soybean lecithin:acrylic resin IV=1:1~3:0.3~0.8:0.2~0.5.

The said high-efficacy, long-acting formulation of silibinin is prepared in the form of tablets or capsules.

A method for preparing the said high-efficacy, long-acting silibinin, comprising the following steps:

step 1. taking silibinin 1 g, povidone K30 1-3 g, soybean lecithin 0.3-0.8 g and acrylic resin IV 0.2-0.5 g and injecting in absolute ethyl alcohol 20-40 ml (70° C. water-bath can be adopted to accelerate dissolution if necessary); after the said materials having dissolved, treating the solution with 60° C. water-bath; then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use;

step 2. taking cyclohexane 20-80 ml, adding in nonyl phenol 10 (NP-10) 4-8 ml and mixing them together; adding in n-hexanol 1-3 ml, 25.6% ammonia water 1-3 ml and agitating for 1 hour at room temperature; slowly dropping in tetraethyl orthosilicate 3-5 ml and agitating for 24 hours at room temperature; adding in absolute ethyl alcohol 40-80 ml and treating with ultrasound for 1 hour; and then centrifugally separating at 15000 rpm for 15 min and washing the precipitate with distilled water three times; adding in some water, freezing and drying the substance in succession, and silica nanoparticles 8 g-32 g are therefore obtained;

taking the said silica nanoparticles 1 g, adding in 0.6 mol/L $Na_2CO_3$ solution 1000 ml, treating with ultrasound for 4-5 min under the condition of 60-70 □, 200 W, and then centrifugally separating at 15000 rpm and washing the precipitate with distilled water three times; adding in distilled water 10 ml, freezing and drying the substance in succession, and mesoporous silica nanoparticles are therefore obtained;

dissolving silibinin 2 g in absolute ethyl alcohol 10-20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silibinin-loaded silica nanoparticles 2 g are therefore obtained, the drug loading rate of which is 51.29~51.77%;

step 3. taking silibinin solid dispersion prepared in step 1 1 g, mixing it with hypromellose K4M 0.2-0.3 g and low-substituted hydroxypropyl cellulose (L-HPC) 0.1-0.2 g, and adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

step 4. taking silibinin solid dispersion prepared in step 1 1 g, mixing it with hypromellose K4M 0.1-0.2 g, low-substituted hydroxypropyl cellulose (L-HPC) 0.2-0.3 g, silibinin-loaded silica nanoparticles prepared in step 2 1.25-2.5 g and mixing them together; adding in some 70% syrup so that a certain soft substance is obtained, sieving the soft substance with 16 mesh and the wet granules so obtained are baked at 60° C. for 30 min, reshaping the granules with 16 mesh and the slow-release granules 2 are therefore obtained;

step 5. mixing the slow-release granules 1 prepared in step 3 and the slow-release granules 2 prepared in step 4 together at the ratio of 1:2.75~1:4; tableting the mixed granules with the force around 40-60 N and the high-efficacy, long-acting tablet of silibinin disclosed in this invention is obtained.

Adopting the said preparation method of the high-efficacy, long-acting formulation of silibinin, mixing the slow-release granules 1 prepared in step 3 and the slow-release granules 2 prepared in step 4 together at the ratio of 1:2.75~1:4; encapsulating the mixed granules and the high-efficacy, long-acting capsule of silibinin disclosed in this invention is obtained.

Beneficial Effects of the Invention

Figure 3:
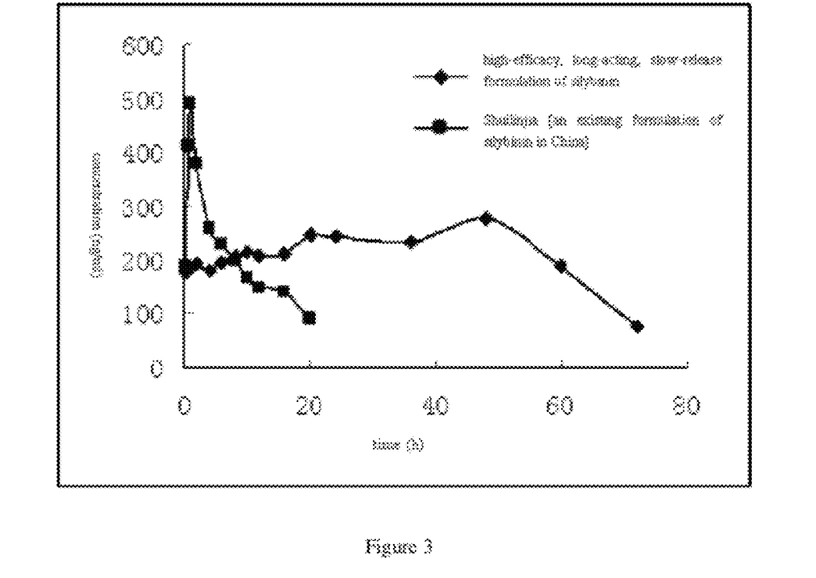
FIG. 3 is the concentration-time curve of the high-efficacy, long-acting, slow-release formulation of silibinin disclosed in this invention when tested in vivo in Beagle dogs.

1. This invention initiates a so-called "triple release" mechanism jointly realized by the quick-release of solid dispersion, the regular slow-release of hydrophilic gel matrix and the long-acting slow-release of mesoporous silica nanoparticles; based on the "double release" method comprising the quick-release technique and the regular slow-release technique, this mechanism fully utilizes the long-acting, slow-release characteristic of the drug-loaded ordered mesoporous material, an advantage resulting from its high absorption due to its high specific surface area and big pore volume; taking ordered mesoporous silica nanoparticles as carrier material and integrating solid dispersion technique, ordered mesoporous nanoparticles technique and hydorphilic gel matrix technique together, a new formulation of silibinin that starts with quick-release, then regular slow-release, and long-acting slow-release at last is prepared, namely, the formulation encompasses quick-release and double slow-release simultaneously. Compared with the existing formulations through in vivo testing in Beagle dogs, the half life of the said high-efficacy, long-acting formulation of silibinin disclosed in this invention is 14.8 times longer while the mean residence time (MRT) of which is 4.52 times longer; the in vivo pharmacokinetic testing in Beagle dogs also indicates that this formulation of siybinin presents a smoother concentration-time curve and reaches a continuous release for 72 hours [see: FIG. 3].

2. This invention combines solid dispersion technique and nanotechnique together; on the one hand, soybean lecithin is added in during the preparation of silibinin solid dispersion, which consequently enhances physical absorption of silibinin; on the other hand, the utilization of nanoparticles technique remarkably enhances the speed and extent of the physical absorption of silibinin, which is contributive to higher bioavailability of the long-acting, slow-release formulation of silibinin as well. Therefore, the silibinin formulation disclosed in this invention is not only a long-acting, slow-release one, but also a formulation of high-efficacy, that is to say, it is a formulation simultaneously presents the double advantages of high-efficacy and long-acting. Compared with the control formulation through in vivo pharmacokinetic testing in Beagle dogs, the relative bioavailability of the long-acting, slow-release formulation of silibinin prepared with the method disclosed in this invention is 383%. In addition, the method disclosed in this invention can be utilized in developing sophisticated, high-efficacy and long-acting drug formulations that need to be administered only once three days.

3. Silica is biological compatible, nontoxic and extensively available; the silica nanoparticles prepared with the method disclosed in this invention have such advantages as simple preparation method, no requirement of special devices, fewer influencing factors during preparation, and higher repeatability.

DETAILED DESCRIPTION OF PREFERRED EMBODIMENTS

The materials and devices required for the following embodiments include:

experiment materials: povidone K30 (Shanghai Shengpu New Materials Co., Ltd.); soybean lecithin (Shanghai Taiwei Pharmaceutical Co., Ltd.); acrylic resin IV (Huainan Shanhe Medical Accessories Co., Ltd.); tetraethyl orthosilicate (Chemical Reagent Co., Ltd. of China National Pharmaceutical Group); hypromellose K4M (Shanghai Colorcon Coating Technology Co., Ltd.); L-HPC (Shanghai Colorcon Coating Technology Co., Ltd); NP-10 (Shanghai Jiafang Trade Co., Ltd.).

experiment devices: rotary evaporator (Heidolph, Germany); H66025 ultrasonic cleaner (Wuxi Ultrasonic Devices Factory); ADP single punch tablet machine (Shanghai Tianxiang Pharmaceutical machinery Co., Ltd.).

Embodiment I

Taking silibinin 1 g, povidone K30 1 g, soybean lecithin 0.2 g and acrylic resin IV 0.1 and injecting in absolute ethyl alcohol 20 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 30 ml, adding in nonyl phenol 10 (NP-10) 4 ml and mixing them together; adding in n-hexanol 1 ml, 25.6% ammonia water 1 ml and agitating for 1 hour at room temperature; slowly dropping in tetraethyl orthosilicate 3 ml and agitating for 24 hours at room temperature; adding in absolute ethyl alcohol 40 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Figure 1:
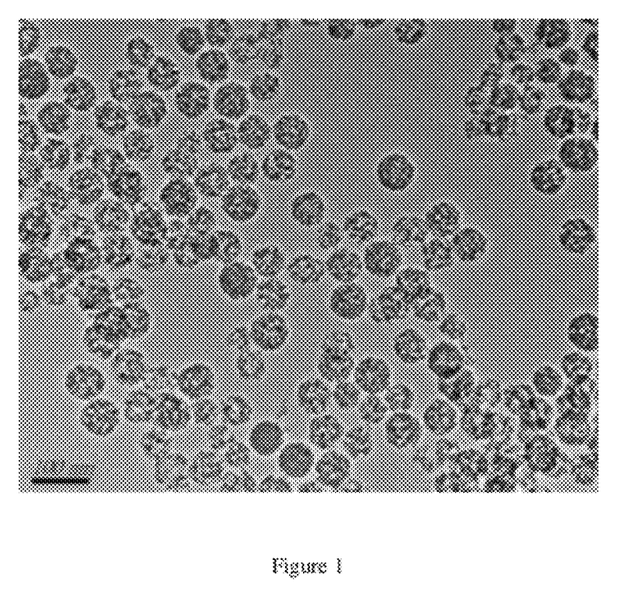
FIG. 1 is a TEM image of the mesoporous silica nanoparticles prepared in this invention.
Figure 2:
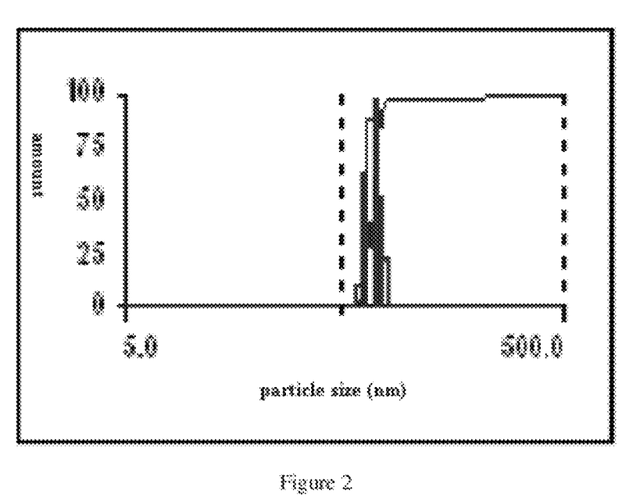
FIG. 2 is the particle size diameter distribution graph of the mesoporous silica nanoparticles prepared in this invention.

Taking the said silica nanoparticles 2 g, adding in 0.6 mol/L $Na_2CO_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm for 15 min and washing the precipitate with distilled water three times; adding in distilled water 1 ml, freezing and drying the substance in succession, and mesoporous silica nanoparticles are therefore obtained [see: FIG. 1 and FIG. 2].

Dissolving silibinin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking silibinin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

Taking silibinin solid dispersion 1.8 g, mixing it with hypromellose K4M 0.36 g, L-HPC 0.4 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:2; and tableting the mixed granules with the force around 40-60 N; the high-efficacy, long-acting tablet of silibinin is therefore obtained.

Embodiment II

Taking silibinin 1 g, povidone K30 3 g, soybean lecithin 0.8 g and acrylic resin IV 0.5 and injecting in absolute ethyl alcohol 40 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 80 ml, adding in nonyl phenol 10 (NP-10) 8 ml and mixing them together; adding in n-hexanol 3 ml, 25.6% ammonia water 3 ml and agitating for 1 hour at room temperature; slowly dropping in tetraethyl orthosilicate 5 ml and agitating for 24 hours at room temperature; adding in absolute ethyl alcohol 80 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 3 g, adding in 0.6 mol/L $Na_2CO_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm for 15 min and washing the precipitate with distilled water three times; adding in distilled water 1 ml, freezing and drying the substance in succession, and mesoporous silica nanoparticles are therefore obtained.

Dissolving silibinin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking silibinin solid dispersion 1.8 g, mixing it with hypromellose K4M 0.4 g and L-HPC 0.4 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

taking silibinin solid dispersion 1.8 g, mixing it with hypromellose K4M 0.36 g, L-HPC 0.4 g and drug-loaded silica nanoparticles 3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained;

Mixing the slow-release granules 1 and the slow-release granules 2 at the ratio of 2:3; and then encapsulating the mixed granules so that the high-efficacy, long-acting, slow-release capsule of silibinin is obtained.

Embodiment III

Taking silibinin 1 g, povidone K30 1.2 g, soybean lecithin 0.4 g and acrylic resin IV 0.3 and injecting in absolute ethyl alcohol 25 ml (70° C. water-bath can be adopted to accelerate dissolution if necessary); after the said materials having dissolved, treating the solution with 60 □ water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 30 ml, adding in nonyl phenol 10 (NP-10) 5 ml and mixing them together; adding in n-hexanol 1.2 ml, 25.6% ammonia water 1.5 ml and agitating for 1 hour at room temperature; slowly dropping in tetraethyl orthosilicate 3.5 ml and agitating for 24 hours at room temperature; adding in absolute ethyl alcohol 50 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 3000 ml, treating with ultrasound for 4 min under the condition of 60° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silibinin 2 g in absolute ethyl alcohol 20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking silibinin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

Taking silibinin solid dispersion 1 g, mixing it with hypromellose K4M 0.1 g, L-HPC 0.3 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and tableting the mixed granules with the force around 40-60 N; the high-efficacy, long-acting tablet of silibinin is therefore obtained.

Embodiment IV

Taking silibinin 1 g, povidone K30 1.5 g, soybean lecithin 0.5 g and acrylic resin IV 0.4 and injecting in absolute ethyl alcohol 30 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 50 ml, adding in nonyl phenol 10 (NP-10) 6 ml and mixing them together; adding in n-hexanol 2.2 ml, 25.6% ammonia water 1.8 ml and agitating for 1 hour at room temperature; slowly dropping in tetraethyl orthosilicate 4.2 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 1000 ml, treating with ultrasound for 5 min under the condition of 65° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silibinin 2 g in absolute ethyl alcohol 20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking silibinin solid dispersion 1 g, mixing it with hypromellose K4M 0.22 g and L-HPC 0.22 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

Taking silibinin solid dispersion 1 g, mixing it with hypromellose K4M 0.15 g, L-HPC 0.25 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and tableting the mixed granules with the force around 40-60 N; the high-efficacy, long-acting tablet of silibinin is therefore obtained.

Embodiment V

Taking silibinin 1 g, povidone K30 2.5 g, soybean lecithin 0.7 g and acrylic resin IV 0.4 and injecting in absolute ethyl alcohol 40 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 70 ml, adding in nonyl phenol 10 (NP-10) 6 ml and mixing them together; adding in n-hexanol 1 ml, 25.6% ammonia water 1.5 ml and agitating for 1 hour at room temperature; slowly dropping in tetraethyl orthosilicate 6 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L Na$_2$CO$_3$ solution 2000 ml, treating with ultrasound for 4.5 min under the condition of 70° C., 200 W, and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silibinin 2 g in absolute ethyl alcohol 15 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and drug-loaded nanoparticles are therefore obtained.

Taking silibinin solid dispersion 1.2 g, mixing it with hypromellose K4M 0.3 g and L-HPC 0.3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

Taking silibinin solid dispersion 1.8 g, mixing it with hypromellose K4M 0.36 g, L-HPC 0.32 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:1; and tableting the mixed granules with the force around 40-60 N; the high-efficacy, long-acting tablet of silibinin is therefore obtained.

Embodiment VI

Taking silibinin 1 g, povidone K30 2 g, soybean lecithin 0.8 g and acrylic resin IV 0.2 and injecting in absolute ethyl alcohol 40 ml (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 60 ml, adding in nonyl phenol 10 (NP-10) 5 ml and mixing them together; adding in n-hexanol 1 ml, 25.6% ammonia water 1.5 ml and agitating for 1 hour at room temperature; slowly dropping in tetraethyl orthosilicate 5.5 ml and agitating for 24 hours at room temperature; adding in absolute ethyl alcohol 70 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L Na$_2$CO$_3$ solution 3000 ml, treating with ultrasound for 4' 20", 4' 10" and 4' under the condition of 60° C. 200 W, 65° C. 200 W and 70° C. 200 W respectively, and then centrifugally separating at 15000 rpm for 15 min and washing the precipitate with distilled water three times; adding in distilled water 1 ml, freezing and drying the substance in succession, and mesoporous silica nanoparticles are therefore obtained.

Dissolving silibinin 2 g in absolute ethyl alcohol 15 ml, soaking mesoporous silica nanoparticles 1 g in the solution for 24 hours, and then centrifugally separating at 15000 rpm for 15 min and washing the precipitate with absolute ethyl alcohol three times; adding in distilled water 1 ml, freezing and drying the substance in succession, and drug-loaded nanoparticles are therefore obtained.

Taking silibinin solid dispersion 1.4 g, mixing it with hypromellose K4M 0.3 g and L-HPC 0.3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

taking silibinin solid dispersion 2.1 g, mixing it with hypromellose K4M 0.42 g, L-HPC 0.48 g and drug-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained;

Mixing the slow-release granules 1 and the slow-release granules 2 at the ratio of 1:1; and tableting the mixed granules with the force around 40-60 N; the high-efficacy, long-acting tablet of silibinin is therefore obtained.

What is claimed is:

1. A formulation of silibinin, comprising:
   a silibinin solid dispersion, silibinin-loaded silica nanoparticles, a slow-release matrix material and a release enhancer, wherein a mass ratio of the silibinin solid dispersion:the silibinin-loaded silica nanoparticles:the slow-release matrix material:the release enhancer is 1:0.5-1.25:0.1-0.3:0.1-0.3;
   wherein the silica nanoparticles are a mesoporous material including a plurality of pores having a diameter of 1.5 nm to 50 nm;
   wherein the silibinin solid dispersion contains povidone K30, soybean lecithin, acrylic resin IV, wherein a mass ratio of silibinin:povidone K30:soybean lecithin:acrylic resin IV is 1:1-3:0.3-0.8:0.2-0.5.

2. The formulation of silibinin as is defined in claim 1, wherein the formulation is prepared in the form of at least one of a tablet and a capsule.

3. The formulation of silibinin in claim 1, wherein silibinin is controllably released over a 72 hour period.

4. A method for preparing a formulation of silibinin, comprising the following steps:
   providing a silibinin solid dispersion;
   preparing a mixture of cyclohexane, nonyl phenol 10 (NP-10), n-hexanol and ammonia water;

dropping in tetraethyl orthosilicate into the mixture;
adding absolute ethyl alcohol to the mixture;
treating the mixture with ultrasound and then centrifugally separating the mixture to obtain silica nanoparticles;
adding a $Na_2CO_3$ solution to the silica nanoparticles;
treating the $Na_2CO_3$ solution with ultrasound to obtain mesoporous silica nanoparticles with a porous diameter between 1.5 nm to 50 nm;
dissolving silibinin in an absolute ethyl alcohol solution;
soaking the mesoporous silica nanoparticles in the absolute ethyl alcohol solution to obtain silibinin-loaded silica nanoparticles;
mixing the silibinin solid dispersion with hypromellose that has a viscosity of 4000 cPs in a 2% aqueous solution, and low-substituted hydroxypropyl cellulose (L-HPC), and dividing the mixture into: (a) a first portion comprising the silibinin solid dispersion, hypromellose that has a viscosity of 4000 cPs in a 2% aqueous solution, and L-HPC, and (b) a second portion comprising the silibinin solid dispersion, hypromellose that has a viscosity of 4000 cPs in a 2% aqueous solution, and L-HPC;
sieving the mixture of (a) the first portion comprising the silibinin solid dispersion, hypromellose that has a viscosity of 4000 cPs in a 2% aqueous solution, and L-HPC to obtain a first set of slow release granules;
mixing (b) the second portion comprising the silibinin solid dispersion, hypromellose that has a viscosity of 4000 cPs in a 2% aqueous solution, and L-HPC with the silibinin-loaded silica nanoparticles to obtain a second set of slow release granules; and
mixing the first set of slow-release granules and the second set of slow-release granules together at a ratio of 1:1 to 1:4.

5. The method for preparing the formulation of silibinin of claim 4, further comprising a step of tableting the mixture of the first set of slow-release granules and the second set of slow-release granules into the form of a tablet.

6. The method of preparing a formulation of silibinin of claim 4, wherein the first set of slow release granules and the second set of slow release granules are encapsulated together in the form of a capsule.

7. The formulation of claim 1, wherein the silica nanoparticles have a specific surface area as high as 1000 $m^2/g$.

8. The formulation of claim 1, wherein a bioavailability of the formulation of silibinin is 383%.

9. A formulation of silibinin, consisting essentially of: a silibinin solid dispersion, silibinin-loaded silica nanoparticles, a slow-release matrix material and a release enhancer, wherein a mass ratio of the silibinin solid dispersion:the silibinin-loaded silica nanoparticles:the slow-release matrix material:the release enhancer is 1:0.5-1.25:0.1-0.3:0.1-0.3;
wherein the silica nanoparticles are a mesoporous material including a plurality of pores having a diameter of 1.5 nm to 50 nm;
wherein the silibinin solid dispersion contains povidone K30, soybean lecithin, acrylic resin IV, wherein a mass ratio of silibinin:povidone K30:soybean lecithin:acrylic resin IV is 1:1-3:0.3-0.8:0.2-0.5.

10. The formulation of claim 9, wherein the silibinin loaded silica nanoparticles have a silibinin loading between 51.29% to 51.77%.

* * * * *

UNITED STATES PATENT AND TRADEMARK OFFICE
CERTIFICATE OF CORRECTION

PATENT NO. : 9,023,388 B2
APPLICATION NO. : 13/126251
DATED : May 5, 2015
INVENTOR(S) : Ximing Xu et al.

It is certified that error appears in the above-identified patent and that said Letters Patent is hereby corrected as shown below:

In the Specification

Column 3, Line 33, delete "60-70 □" and insert --60-70° C.--

Column 7, Line 19, delete "60 □" and insert --60° C.--

Signed and Sealed this
Eighth Day of December, 2015

Michelle K. Lee
*Director of the United States Patent and Trademark Office*